United States Patent [19]

Kolesar, Jr.

[11] Patent Number: 4,549,427
[45] Date of Patent: Oct. 29, 1985

[54] ELECTRONIC NERVE AGENT DETECTOR

[75] Inventor: Edward S. Kolesar, Jr., Austin, Tex.

[73] Assignee: The United States of America as represented by the Secretary of the Air Force, Washington, D.C.

[21] Appl. No.: 533,331

[22] Filed: Sep. 19, 1983

[51] Int. Cl.⁴ .......................................... G01N 31/06
[52] U.S. Cl. ........................................ 73/23; 422/88; 436/104
[58] Field of Search ................ 73/23; 422/83, 88, 90, 422/98; 436/104, 902

[56] References Cited

U.S. PATENT DOCUMENTS

| | | | |
|---|---|---|---|
| 3,375,700 | 4/1968 | Hubner | 73/23 |
| 3,421,106 | 1/1969 | Garber et al. | 331/40 |
| 3,451,901 | 6/1969 | Seiger et al. | 422/98 X |
| 3,895,912 | 7/1975 | Naumann | 23/255 E |
| 4,193,964 | 3/1980 | John | 422/90 |
| 4,260,884 | 4/1981 | Lovelock | 422/98 X |
| 4,361,026 | 11/1982 | Muller et al. | 73/23 |

OTHER PUBLICATIONS

Janata et al.; Chemically Sensitive Field-Effect Transistor Chemical Warfare Agent Detector; USAF, SAM-TR-82-10, Apr. 1982.
K. E. Petersen, Micromechanical Membrane Switches on Silicon, IBM J. Res. Develop., vol. 23, No. 4, Jul. 1979, pp. 376 to 384.
G. G. Guilbault et al., A Coated Piezoelectric Crystal to Detect Chemical Warfare Agents in Aircraft, Report SAM-TR-80-21, Jul. 1980.
R. J. Wilfinger et al., The Resonistor: A Frequency Selective Device Utilizing the Mechanical Resonance of a Silicon Substrate, IBM Journal, Jan. 1968, pp. 113-118.
Janata et al., Field-Effect Transistors to Detect Chemical Warfare Agents in Aircraft, USAF, SAM-TR-80-25, Aug. 1980.
Janati et al., Chemically Sensitive FET to Detect Organophosphorous Compounds and Pesticides, Aviation, Space, and Env. Medicine, Nov. 1981.

Primary Examiner—David L. Lacey
Assistant Examiner—Michael S. Gzybowski
Attorney, Agent, or Firm—Donald J. Singer; Stanton E. Collier

[57] ABSTRACT

A personal field chemical warfare nerve agent detector has therein a transducer having two micromechanical cantilever oscillators. One of the cantilever oscillators has deposited, as an end-mass, a chemically selective substance on the cantilever. The nerve agent if present causes the natural resonant frequency to change. The changed resonant frequency is compared to a reference resonant frequency of the other cantilever oscillator without an end-mass. The amount of frequency change indicates the presence of a chemical nerve agent.

1 Claim, 9 Drawing Figures

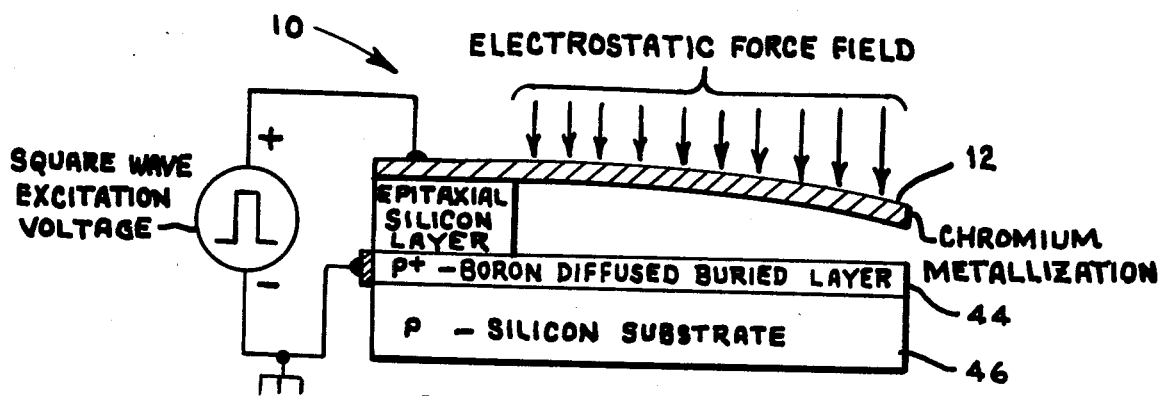
FIG. 1
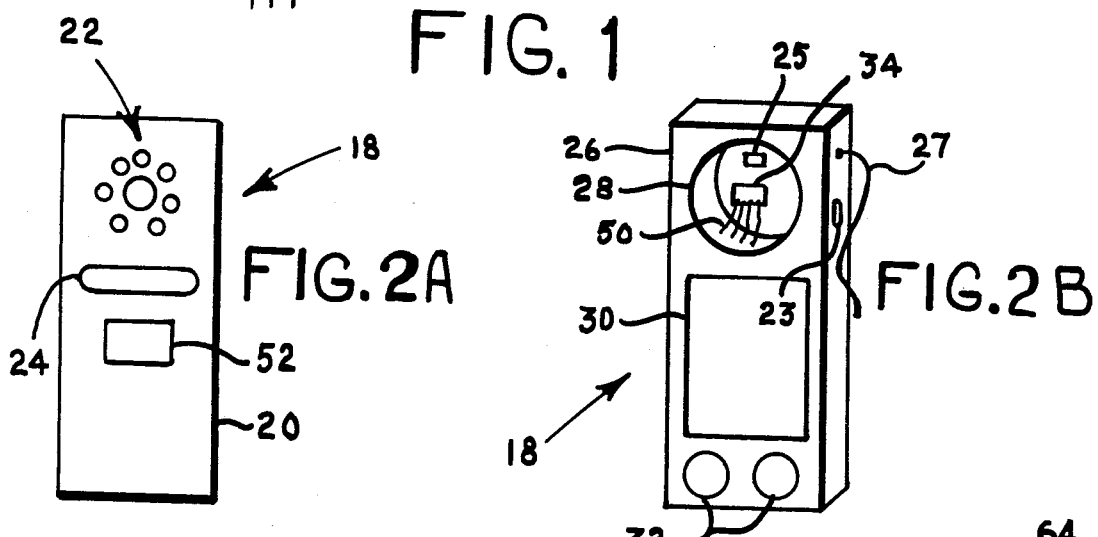
FIG. 2A
FIG. 2B
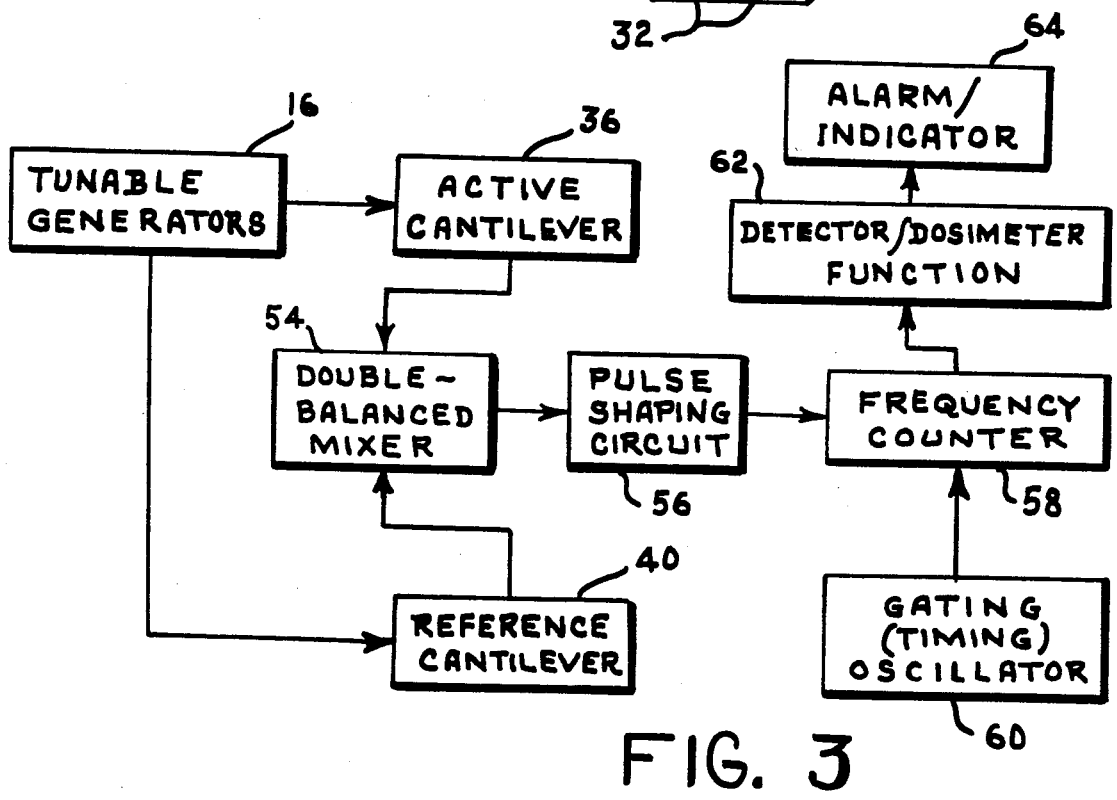
FIG. 3

ELECTRONIC NERVE AGENT DETECTOR

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to nerve agent detectors, and, in particular, relates to a real-time monitoring device for detecting organophosphorous chemical warfare nerve agents.

Presently, the only personal detector for nerve agents is a litmus type paper that is issued to GIs when in areas of potential danger. Nerve agents that are applied in a gaseous form, invisible to the eye, obviously would not be detected until it was too late. The only warning would be the presence of bodies without injuries in an area. Typically, nerve agents are applied in an aerosol form from a bursting ordinance round or sprayed from an aircraft. The droplets would be found on the surface of clothing, vehicles, aircraft, etc. The litmus type paper is rubbed against the surface and if the particular agent is present, the paper changes color. Based upon the type of nerve agent found, the proper antidote can be administered. Given the proper warning, chemical warfare clothing can be used for protection until the agent is removed or neutralized. The above warnings such as dud sounding ordinance, fog in low lying areas, stricken personnel, aircraft spraying may come too late for the GI in the field away from area electronic agent detectors.

There are presently electronic nerve agent detectors that are able to detect various agents but these are very expensive, large, issued only to large combat units, and to bases. These are used as area detectors to protect GIs massed in a camp, a base, etc. and are totally useless to a GI in the field.

These drawbacks have motivated a search for alternative devices.

SUMMARY OF THE INVENTION

The present invention overcomes the problems encountered in the past and described in detail hereinabove by providing a personal nerve agent detector/dosimeter.

The basic detector has a housing for holding and protecting an electronic circuit and a pair of deflectable micromechanical cantilevers driven by oscillators.

One of the pair of cantilevers is coated with a chemically selective substance to form an end-mass load. As the nerve agent of concern is absorbed by the selective substance, the end-mass changes and so does the resonant frequency of that coated cantilever. The uncoated cantilever acts as a standard frequency source to which the coated cantilever is compared.

These frequencies are input to mixer circuit that outputs the difference frequency. The difference frequency after going through pulse shaping is input to counter circuits that determine if a set limit is exceeded and, if so, how much is the limit exceeded by as a function of time.

Further, additional pair of cantilevers can be added that are able to detect different nerve agents.

It is therefore an object of the present invention to provide a personal nerve agent detector.

It is a further object of the present invention to provide for a nerve agent detector that operates continuously and on a real-time basis.

It is a further object of the present invention to provide for a nerve agent detector that is able to detect a wide variety of nerve agents, specifically organophosphorous agents.

It is a further object of the invention to provide for a nerve agent detector that is not affected by physical/environmental interferences.

It is a further object of the present invention to provide for a detector that functions as a dosimeter.

These and many other objects and advantages of the present invention will be readily apparent to one skilled in the pertinent art from the following detailed description of a preferred embodiment of the invention and related drawings.

BRIEF DESCRIPTION OF THE DRAWINGS

FIG. 1 is a schematic representation of one micromechanical cantilever;

FIGS. 2A to 2B are diagramatic representations of a housing for the detector of the present invention;

FIG. 3 is a functional block diagram of the electronic circuit required to operate the detector of the present invention;

DETAILED DESCRIPTION OF THE PREFERRED EMBODIMENT

Figure 4A:
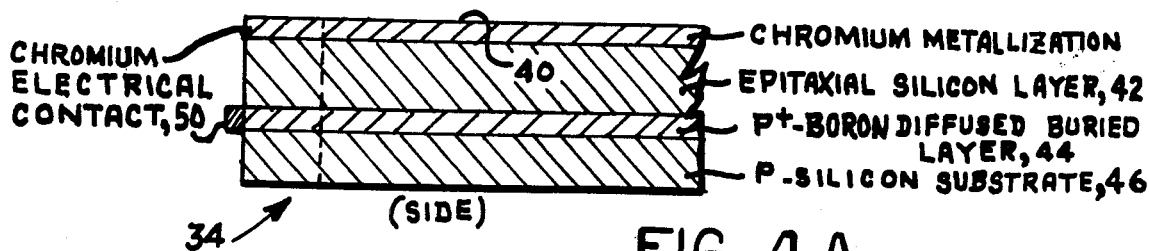
FIGS. 4A, 4B, and 4C are cross sectional views of the micromechanical cantilevers of the detector of the present invention.
Figure 4B:
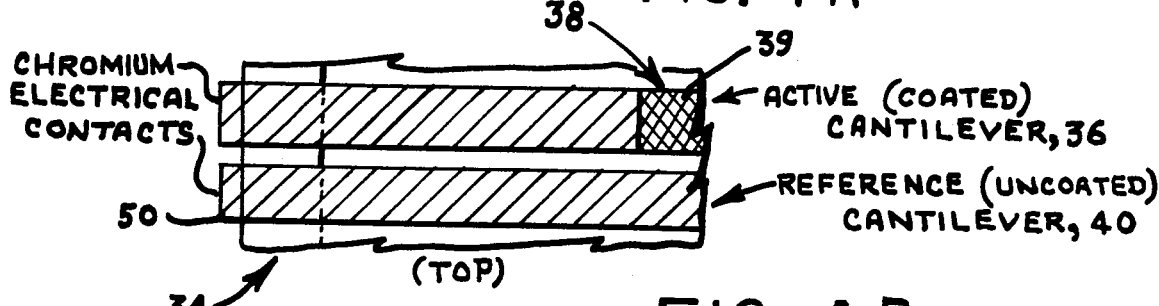

Reference is now made to FIG. 1 of the drawings which illustrates a cantilever oscillator 10. As a pulsed voltage is applied to a cantilever 12 and a conducting layer 44, cantilever 12 is drawn to layer 44 until the voltage is removed at which time cantilever 12 will oscillate in a fixed-free mode at its natural frequency given by equation I, $$fr = \frac{1}{2\pi}\left[\frac{EBH^3}{4L^3(0.23Mc)}\right]^{\frac{1}{2}} \quad (I)$$

where
fr = cantilever's mechanical resonant frequency
E = cantilever's Young's modulus
B = cantilever's width
H = cantilever's thickness
L = cantilever's length
Mc = cantilever's mass but for the purpose of detecting chemicals, a chemically selective substance 39, FIG. 4B, is added to the tip of cantilever 12 to form an end-mass 38, FIG. 4B, thus causing the frequency to be given by equation II, $$fr = \frac{1}{2\pi}\left[\frac{EBH^3}{4L^3(Me + 0.23Mc)}\right]^{\frac{1}{2}} \quad (II)$$

where Me = cantilever's end mass.

In order to obtain a stable operating point with maximum output, the drive frequency output from a tunable generator 16, shown in FIG. 3, is selected to match the resonant frequency given by equation II.

A detector 18 shown in FIG. 2A has a cover 20 having air ports 22 and a sound port 24. A case 26 on to which cover 20 attaches is shown in FIG. 2B. Case 26 has a detector section 28, an electronics section 30, and a power section 32.

Inside detector section 28 is a dual cantilever transducer 34 shown in a partial top view in FIG. 4B. Transducer 34 has therein an active cantilever 36 with chemically active end-mass 38 along with a reference cantilever 40. Active cantilever's 36 end-mass 38 acts to mechanically load cantilever 36 and reduces its resonant frequency as the nerve agent reacts with chemically selective substance 39. Although only a single pair of cantilevers are in transducer 34, additional pairs can easily be fabricated and have different chemically selective substances 39 thereon.

Figure 5A:
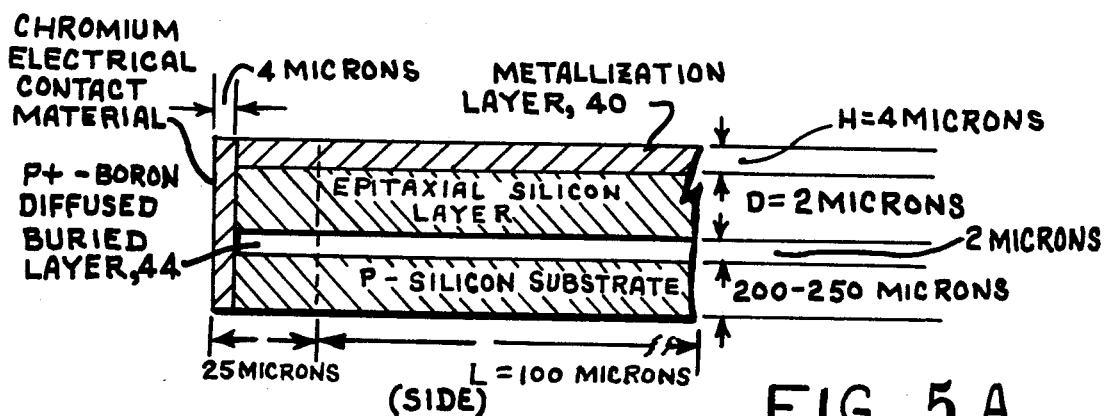
FIGS. 5A and 5B show typical dimensions associated with a pair of cantilevers of the present invention.
Figure 5B:
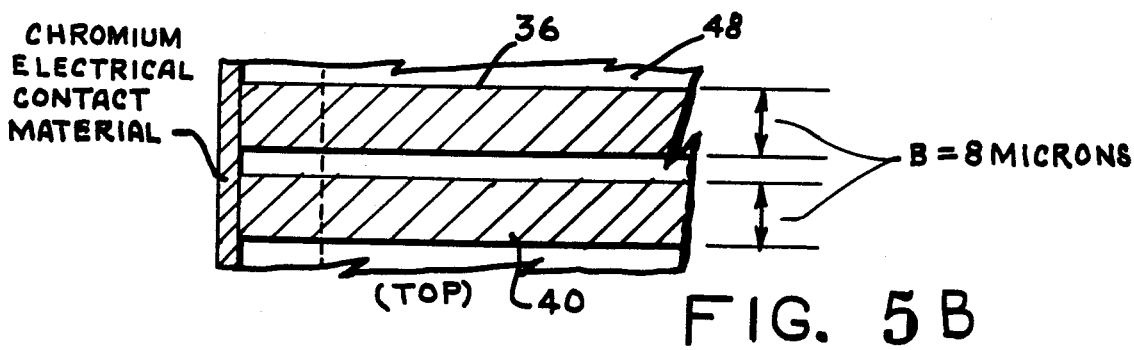

If one applies a square voltage pulse to transducer 34, it is related to the dimensions as given in equation III.

$$V_{pp} \cong \left[ \frac{3EH^3D^3}{10\epsilon_o L^4} \right]^{\frac{1}{2}} \quad \text{(III)}$$

where
$V_{pp}$=applied square-wave peak-to-peak voltage
D=distance from the underside of the cantilever to the top of the p+-layer in the well.
$\epsilon_o$=permittivity of free space.
FIGS. 5A and 5B illustrate typical dimensions.

As an example, if chromium is used to make cantilevers 38 and 40, FIG. 4B, and the dimensions given in FIGS. 5A and 5B are used in Equation (I) to (III), the performance of transducer 34 can be predicted. For reference cantilever 40, Equation I predicts fr=331861 Hertz with $V_{pp}$=55 volts with an end-mass 38 of 10 picograms with 1 picogram. With 1 picogram of nerve agent absorbed therein, Equation II predicts fr=331548. Thus, one is able to have a frequency change of 31 Hertz if a picogram of nerve agent is absorbed on a 10 picogram end-mass 38.

The construction of cantilever oscillator 10 of FIG. 1 is similar to the construction of micromechanical membrane switches disclosed in the article by K. E. Petersen, entitled "Micromechemical Membrane Switches on Silicon" in IBM J.RES. DEVELOP, Vol. 23, No. 4 of July 1979 on pages 376 to 384.

Figure 4C:
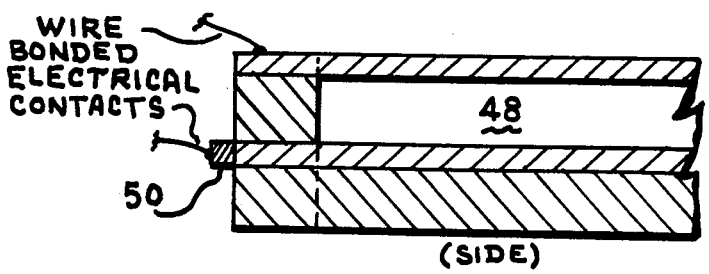

FIG. 4A, 4B, and 4C show one arrangement of cantilevers 36 and 40 of transducer 34. A substrate 46 surrounding transducer 34 has been removed except for the part shown.

Reference cantilever 40 of FIG. 4A is made of a metal such as chromium which is plated on an epitaxial silicon layer 42. A P+-boron diffused buried layer 44 acts as an etch stop and is deposited on top of a silicon substrate 46.

Once the appropriate layers are deposited as shown in FIG. 4A, standard etching techniques using a photo mask produce cantilevers 36 and 40 on the top surface of layer 42 as shown in FIG. 4B without the chemically active end mass 38 which is added later.

In order to produce a well 48 shown in FIG. 4C beneath cantilevers 36 and 40, layer 42 must be removed by controlled etching.

A typical silicon etchant (EDP) is a hot (118° C.) solution of ethylene diamine, pyrocatechol, and water. This etchant is desirable since it is anisotropic etchant of silicon, does not attack chromium, and is greatly retarded by boron highly doped silicon thus acting as an etch stop. Since the anistropic etching behavior of EDP permits control over the extent and direction of lateral etching, p+-buried layer 44 is used as an etch stop thus effectively resulting in a completely self-limiting etching step since it does not attack the patterned chromium.

As an example, a conventional p-silicon wafer (200–250 microns thick and 2.5 centimeters in diameter) is highly doped with boron to form about a 2 micron thick p+-boron diffused buried layer 44. An epitaxial layer of silicon is grown over layer 44 in a conventional manner to form layer 42 to a depth of about 2 microns. Chromium is deposited on the sides and top to a depth of about 4 microns. Cantilevers 36 and 40 and chromium electrical contacts 50 in FIG. 4B are formed as noted above to produce two similarly constructed cantilever oscillators 10. After this, well 40 is formed. The outer edges of the pattern are not undercut because the etching mask 10 is aligned along the silicon (100) crystal plane direction. Substrate 46 is bonded to a ceramic header, not shown, with epoxy. The exitation voltage leads are attached between the chromium points and package pads by stitch bonding using 25 micron diameter gold wire.

Chemically active end-mass 38 of active cantilever 36 of FIG. 4B is a thin film of chemically selective substance 39 selected from the following group which has been determined to be responsive to, in particular, organophosphorous chemical warfare nerve agents:
(1) L-histidine hydrochloride
(2) DL-histidine hydrochloride
(3) Succinylcholine chloride
(4) Succinylcholine iodide
(5) 1-dodecyl-2-hydroximinomethylphridinium iodide (2-PAD)
(6) Ternary mixture of 1-n-dodecyl-3-hydroximinomethylpyridinium iodide (3-PAD) (31 percent); sodium hydroxide (13 percent); and Triton X-100 (55 percent)
(7) XAD-4-$Cu^{2+}$-diamine
(8) Cu (Butyrate)$_2$. Ethylenediamine
(9) PVBC - Triethylenetetraamine - $Cu^{2+}$- Chloride
(10) PVBC - Tetramethylethylenediamine - $Cu^{2+}$- Chloride
(11) PVP - Tetramethylenediamine - $Cu^{2+}$- Chloride
(12) PVP - Triethylenetetraamine - $Cu^{2+}$- Chloride
(13) PVP - 2,2'- Bipyridine - $Cu^{2+}$- Chloride
where PVBC is Poly-vinylbenzyl chloride and PVP is Polyvinylphrolidone.

Clearly, other chemically selective compounds found to be reactive to selected nerve agents can be applied to additional sets of transducers 34 mounted in detector section 28.

Various methods are available to deposit the above chemicals such as vacuum deposition, dipping, spraying, electro deposition, or dropping with a microsyringe. For example, with the aid of a microscope, dropping with a microsyringe is implemented by dropping a solution of chemically selective substance 39 with volatile solvent (20 percent of n-propyl alcohol or methanol) on the top surface of active cantelever 36 as end-mass 38. Transducer 34 is placed in an oven at 60° C. for about 2 hours to evaporate the solvent and leave a thin film of substance 39. The actual mass of deposited substance 39 can be verified by measuring the resonant frequency of active cantilever 36 and using Equation II. Several trials permit the user to determine the volume of the microsyringe drop to be used to deposit a known thin film mass.

For purposes of discussion, only one transducer 34 is mounted in detector section 28. Mounting and connecting additional transducers 34 would use conventional techniques as explained above. An indicator 52 mounted on cover 20 of case 26 would indicate which nerve agent is present.

Transducer 34 is mounted to case 26, FIG. 2B, by conventional means such as epoxy with silicone grease to ensure efficient thermal contact. Leads 50 connect electrically transducer 34 to electronic section 30 which, for one transducer 34, has integrated circuits to perform the functions noted in FIG. 3.

Since transducer 34 must be protected from dust, water, etc to a certain degree, transducer 34 is mounted within detector section 28 having an internal dead volume of about 80 microliters. External air is drawn into input air port 22 having a one-way diaphram valve and filter, not shown, over transducer 34, and out output air port 23 having also a one-way valve. Air flow is continuous and induced by a diaphragm air pump 25 mounted within detector section 28. Air ports 22 and 23 can be mounted in other positions, the ones shown being only an example. Case 26 and cover 20 can be made of metal to electrically insulate to a high degree the components therein from external signals. A means of attaching detector 18 to a user can be a clip 27.

Referring to FIG. 3, tunable generator 16 outputs frequencies equal to the resonant frequency of active cantilever 36 and reference cantilever 40. Because of the similarity of construction, environmental changes should produce equal changes in the resonant frequencies output from cantilevers 36 and 40. A double balanced mixer 54 subtracts the resonant frequencies of cantilevers 36 and 40 and outputs a difference frequency to pulse shaping circuit 56. Pulse shaping circuit 56 conditions the difference frequency signal for input into a frequency counter 58. Frequency counter 58 is repeatedly initiated by gating oscillator 60. Frequency counter 58 outputs a frequency difference signal to detector/dosimeter 62 wherein a change in the frequency difference signal indicates presence of nerve agent and the sum of changes indicates the accumulated dose received.

Clearly, many modifications and variations of the present invention are possible in light of the above teachings and it is therefore understood, that within the inventive scope of the inventive concept, the invention may be practiced otherwise than specifically claimed.

What is claimed is:

1. A chemical warfare nerve agent detector comprising:

a container having a cover and a case, said container having therein input and output air ports for circulating air through a detector section, an alarm port, an indicator display, an electronics section comprising electronic means, a power section, and said container having attaching means whereby said detector can be worn by a person;

at least one transducer mounted within said detector, said at least one transducer having an active cantilever oscillator and a reference cantilever oscillator, each of said at least one transducers having cantilevers essentially similarly shaped so that their natural resonant frequencies are closely matched, said cantilevers being electrically connected to said electronic means for detecting and measuring their oscillation frequencies, said cantilevers being mounted over a rectangular shaped well, the sides of said well comprising an insulating layer, the bottom of said well comprising a highly doped layer of semiconductor material, said highly doped layer being electrically connected to said electronic means, said highly doped layer being deposited on a silicon substrate that is mounted in said detector section, said active cantilever oscillator being chemically absorptive to a chemical agent by absorbing said chemical agent on a chemically selective substance attached to said active cantilever and said active cantilever being composed of metallic material, said reference cantilever oscillator having a reference cantilever being composed of metallic material, said chemically selective substance being a chemical composition selected from the group consisting of:

(1) XAD-4-$Cu^{2+}$-diamine;
(2) Cu (Butyrate)$_2$. Ethylenediamine;
(3) PVBC - Triethylenetetraamine - $Cu^{2+}$- Chloride;
(4) PVBC - Tetramethylethylenediamine - $Cu^{2+}$- Chloride;
(5) PVP - Tetramethylenediamine - $Cu^{2+}$- Chloride;
(6) PVP - Triethylenetetraamine - $Cu^{2+}$- Chloride; and
(7) PVP - 2, 2'- Bipyridine - $Cu^{2+}$- Chloride;

an air pump for causing an air flow through said detector section and over said at least one transducer in said detector section; and said electronic means further comprising means for detecting the absorption of said chemical agent on said active cantilever wherein the frequency of said active cantilever is compared to the frequency of said reference cantilever, said electronic means measuring the amount of said chemical agent absorbed on the active cantilever by comparing the differences in frequencies between said active cantilever oscillator and said reference cantilever oscillator, said electronic means mounted in said electronic section, and electrically connected to said transducer, an alarm, and said indicator display and batteries for supplying electric power, said batteries being removably mounted in said power section.

* * * * *